(12) United States Patent
Skelton

(10) Patent No.: US 6,875,985 B2
(45) Date of Patent: Apr. 5, 2005

(54) ELECTOMAGNETIC DETECTION APPARATUS

(75) Inventor: Colin David John Skelton, Essex (GB)

(73) Assignee: NDC Infrared Engineering Limited, Maldon Essex (GB)

(*) Notice: Subject to any disclaimer, the term of this patent is extended or adjusted under 35 U.S.C. 154(b) by 2 days.

(21) Appl. No.: 10/227,553

(22) Filed: Aug. 22, 2002

(65) Prior Publication Data

US 2004/0036024 A1 Feb. 26, 2004

Related U.S. Application Data

(63) Continuation of application No. PCT/GB00/00745, filed on Mar. 2, 2000.

(51) Int. Cl.⁷ .............................................. G01N 21/17
(52) U.S. Cl. ................. 250/341.1; 250/340; 250/341.7; 250/341.8
(58) Field of Search ........................ 250/252.1, 339.03, 250/339.1, 339.11, 341.1, 341.5, 341.7, 341.8, 350, 354.1

(56) References Cited

U.S. PATENT DOCUMENTS

| | | | | |
|---|---|---|---|---|
| 3,870,884 A | * | 3/1975 | Williams | ............... 250/339.11 |
| 4,412,744 A | | 11/1983 | Lee et al. | |
| 6,281,498 B1 | * | 8/2001 | Fellows | ................. 250/339.06 |

FOREIGN PATENT DOCUMENTS

| | | | |
|---|---|---|---|
| EP | 0 558 854 A1 | 9/1993 | |
| EP | 0 818 675 A2 | 1/1998 | |
| GB | 1 401 699 | 7/1975 | |
| GB | 1401699 | * 7/1975 | ............. G01J/1/42 |
| GB | 2 347 210 | 8/2000 | |
| WO | 98/22806 | 5/1998 | |

* cited by examiner

*Primary Examiner*—Brian Healy
*Assistant Examiner*—Christopher M. Kalivoda
(74) *Attorney, Agent, or Firm*—Katten Muchin Zavis Rosenman

(57) ABSTRACT

An infrared absorption gauge includes a detector circuit including a detector for detecting electromagnetic radiation from a sample and for generating a signal representing the radiation received, and means for stabilizing a response characteristic of the detector to the radiation detected thereby, said stabilizing means having a GaAs diode for directing radiation at the detector and means for controlling the radiation source in dependence upon the signal generated by the detector. The stabilizing means thus acts as a negative feedback loop and seeks to maintain the overall illumination irradiating the detector (i.e. the combined illumination that is reflected back from the sample and that is emitted by the GaAs diode), at a substantially constant predetermined level, which tends to linearize and extend the frequency response of the detector to the radiation detected.

17 Claims, 4 Drawing Sheets

ELECTOMAGNETIC DETECTION APPARATUS

CROSS-REFERENCE TO RELATED APPLICATION

The present application is a continuation of International Patent Application PCT/GB00/00745, filed on Mar. 2, 2000, which is hereby incorporated by reference.

TECHNICAL FIELD

The present invention relates to electromagnetic detection apparatus, and in particular to an electromagnetic gauge for measuring a parameter of a sample, especially an infrared absorption gauge.

BACKGROUND ART

Infrared absorption gauges are well known and are used for example for measuring constituents of samples (e.g. the moisture content of paper or tobacco, or the fat, protein and water contents of foodstuffs), the amounts of substances absorbed or adsorbed on a substrate, the thickness of coatings or films on a substrate or the degree of cure of resins in a printed circuit board. In this specification, the term "parameter" is used to denote the property (composition, coating thickness etc.) of the sample being measured.

Infrared absorption gauges conventionally operate by projecting infrared radiation at two or more wavelengths onto a sample or a substrate and measuring the intensity of the radiation reflected, transmitted or scattered by the sample. Signals proportional to the measured intensity are processed to provide a value of the parameter being measured. At least one of the two or more wavelengths projected by the gauge is chosen to be absorbed by the parameter of interest while at least one other wavelength is chosen to be substantially unaffected by the parameter of interest. For example, when measuring the amount of water in a sample, one of the wavelengths (the "measuring wavelength") can be chosen at an absorption wavelength of water (either 1.45 micrometer or 1.94 micrometer) and the other wavelength (known as the "reference wavelength") is chosen to be one that is not significantly absorbed by water.

Generally, gauges include an infrared radiation source having a broad emission spectrum and a detector for receiving radiation reflected, scattered or transmitted by the sample; filters are placed between the source and the sample to expose the sample only to the desired measuring and reference wavelengths; in this case, the sample is successively exposed to radiation at the selective wavelengths, e.g. by placing appropriate filters on a rotating wheel in front of the radiation source. Alternatively, the filter wheel can be placed between the sample and the detector and each filter is successively interposed between the sample and the detector. Naturally, if the source can produce radiation of the desired wavelength without the use of filters, then such filters can be dispensed with.

The detector measures the intensity of light after interaction with the sample and produces a signal according to the intensity of the radiation incident upon it. In the most simple case, by calculating the ratio between the signal from the detector when receiving light at the measuring wavelength to that when receiving light at the reference wavelength, a signal can be obtained that provides a measure of the parameter concerned, for example the amount of moisture in a sample. Often, several measuring wavelengths and/or several reference wavelengths are used and the signals of the measuring wavelengths and of the reference wavelengths are used to calculate the parameter concerned.

The detectors which are normally used in such measuring gauges are conventionally lead sulphide (PbS) detectors, because they display better detectivity and wavelength response than most other detectors which might be employed in such applications. However, PbS detectors have a number of limitations, including particularly the following:

(a) Temperature sensitivity: the resistance of a typical detector cell falls by 25% for every 10° C. rise in temperature.

(b) Non-linearity: the response of the detector to incident radiation is not linear over the whole operational range of the detector.

(c) Response time: the response time of the detector usually limits the rate at which different wavelengths can be detected, that is the rate at which successive filters can be employed. Faster filter data rates tend to result in the signal from the wavelength obtained from one filter lagging so much that it bleeds into that from the wavelength obtained from the next filter, thereby causing "cross-talk".

(d) Noise: at low frequencies of operation of the detector a type of noise known as 1/f noise predominates. If a relatively low filter data rate is chosen to avoid crosstalk, then such noise becomes a problem.

It is apparent from the, above that the detectors currently used in measuring gauges suffer from a number of drawbacks, not the least of which is their response time.

The present invention seeks to address these problems and to improve the performance of the detectors employed in electromagnetic detection apparatus, such as infrared measuring gauges.

DISCLOSURE OF INVENTION

According to one aspect of the present invention, there is provided an electromagnetic detection apparatus comprising:

a detector circuit including a detector for detecting electromagnetic radiation and for generating a signal representing the radiation received, and means for stabilising a response characteristic of the detector to the radiation detected thereby, said stabilising means comprising:

a controlled source of electromagnetic radiation for directing radiation at the detector, and means for controlling the radiation source in dependence upon the signal generated by the detector.

In a preferred form of the invention, the means for stabilising a response characteristic of the detector are arranged to achieve at least one of the following: linearisation of the detector response and/or extension of the frequency of the response of the detector.

In an infrared measuring gauge, improvement of the linearity tends to enhance the temperature stability of the measuring gauge and lead to more predictable calibration. Extension of the detector frequency response permits the use of much faster filter data rates, and thus reduces the response time of the measuring gauge. Faster filter speeds also result in reduced ambient light sensitivity and can lead to improvements in noise.

Advantageously, the means for controlling the radiation source are arranged to adjust the intensity of the radiation emitted by this source.

In one embodiment of the invention, the controlling means are arranged to adjust the intensity of the radiation emitted by the radiation source in order to maintain the detector signal at a substantially predetermined level.

In another embodiment of the invention, the controlling means are arranged to adjust the intensity of the radiation emitted by the radiation source in order to minimise variations in the detector signal.

Advantageously, a feedback path is provided from the output of the detector circuit to the second radiation source for this purpose.

BRIEF DESCRIPTION

The invention is described further, by way of example, with reference to the accompanying drawings, in which.

MODES FOR CARRYING OUT THE INVENTION

Figure 1:
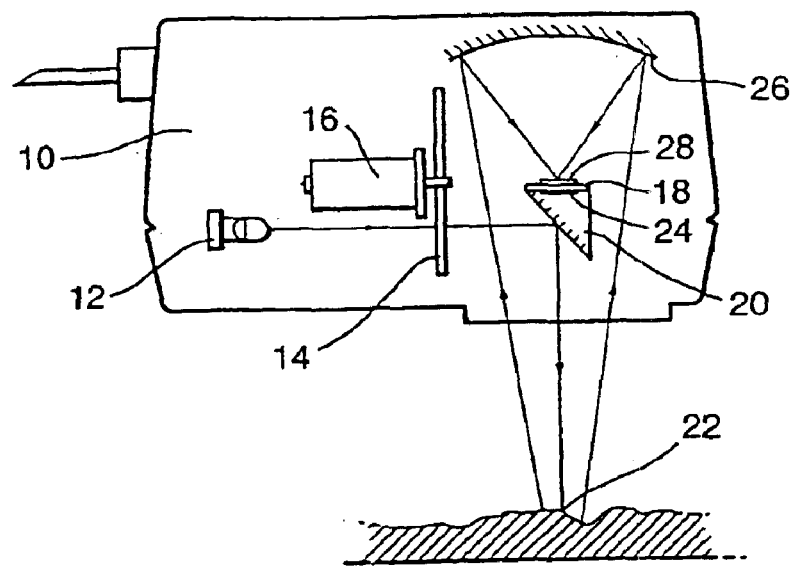
FIG. 1 is a schematic section through the head of a known infrared gauge, for the purposes of explanation.

Referring initially to FIG. 1, this shows the head 10 of a known infrared gauge, for example as described in our published PCT application No. WO98/22806. The head 10 contains a lamp 12 providing a source of infrared radiation, and a circular filter wheel 14 driven by a motor 16. The filter wheel 14 carries a series of filters, for example 5 filters, and each filter is designed to pass a different selected emission Wavelength. The light passed by the respective filters is directed towards a detector mounting table 18, as described below.

The mounting table 18 carries a beam splitter 20 which reflects a portion of the light beam downwardly out of the infrared gauge 10 towards a sample 22. A remaining portion of the infrared light beam striking the beam splitter 20 is refracted within the beam splitter towards a detector assembly 24 including a photo-electric sensor. Meanwhile, the light emitted by the head 10 towards the sample 22 is reflected back from the sample 22 towards a collecting mirror 26 in the head 10 and thence to another detector assembly 28 including another photo-electric sensor. The two detector assemblies 24, 28 thus generate detection signals representing, respectively, the intensity of the light emitted by the lamp 12 and filtered by a selected one of the filters, and the intensity of that same light after reflection from the sample 22. The detector assembly 28 is normally referred to as the primary detector assembly and the detector assembly 24 is normally referred to as the secondary detector assembly. The signals generated by the two detector assemblies 28, 24 are processed in a known manner to provide a measurement of a parameter of the sample 22.

Figure 2:
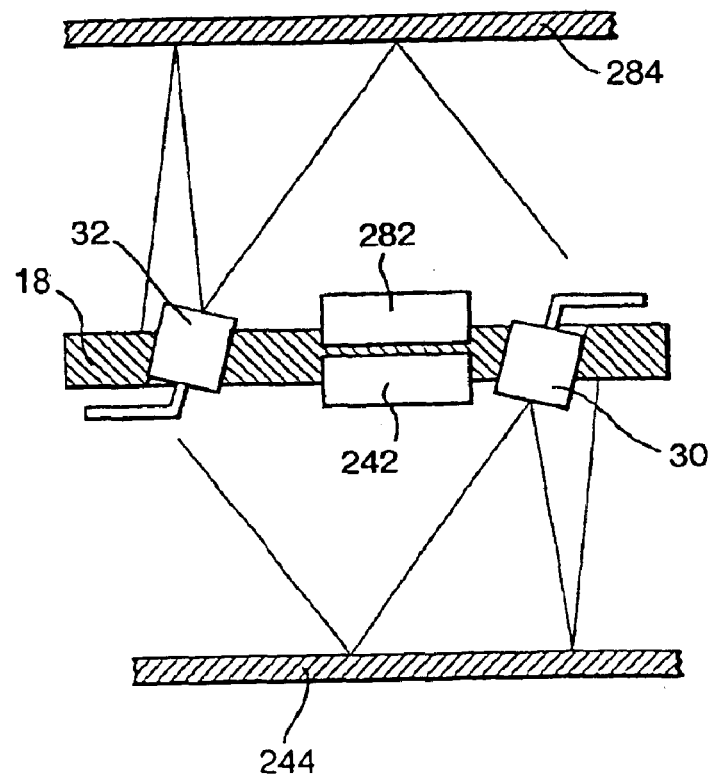
FIG. 2 is a detailed schematic section through a detector mounting plate of such an infrared gauge, but illustrating the present invention.

The measuring gauge described thus far is known as a back-scatter gauge in that the light which is detected is scattered back from the sample whose parameter is to be measured. Another known measuring gauge detects the light that is transmitted through a sample whose parameter is to be measured Turning now to FIG. 2, this shows a detector arrangement according to the present invention having a mounting table 18 bearing a primary detector assembly 28 and a secondary detector assembly 24 as shown in FIG. 1. As is known, the primary detector assembly 28 features a PbS detector 282 and a blocking filter 284, which is a small sheet of silicon, mounted in front of the detector 282 in order to block out visible light. Likewise, the secondary detector assembly 24 features a PbS detector 242 and a blocking filter 244, also a small sheet of silicon, mounted in front of the detector in order to block out visible light.

In accordance with the invention, however, the mounting table 18 also bears additional sources of radiation, in this instance a first Gallium Arsenide (GaAs) infrared emitter or diode 30 directed towards the blocking filter 244 and a second GaAs diode 32 directed towards the blocking filter 284. The GaAs diode 30 directs infrared radiation towards the blocking filter 244, and such radiation is reflected back by the blocking filter 244 towards the mounting table 18 and irradiates the detector 242 in use. Similarly, the GaAs diode 32 directs radiation towards the blocking filter 284 and such radiation is reflected back towards the mounting table 18 and irradiates the detector 282 in use. Consequently, during operation of the measuring head 10, the primary and secondary detectors 282, 242 are receiving not only the successively applied measuring and reference wavelengths, but also the radiation from the two GaAs diodes 32, 30. The two GaAs diodes 32, 30 are arranged to co-operate with the detectors 282, 242 in such a manner as to stabilise the outputs from these detectors, and for this purpose the intensity of the radiation emitted by the diodes 32, 30 is controlled in a manner to be described below.

Figure 3:
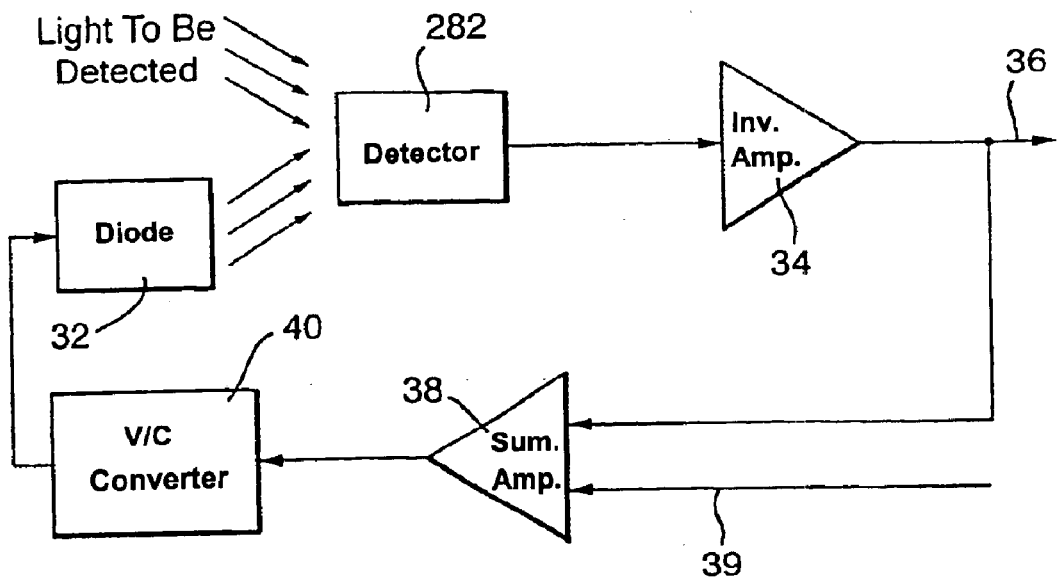
FIG. 3 is a block diagram showing one embodiment of the present invention.
Figure 4:
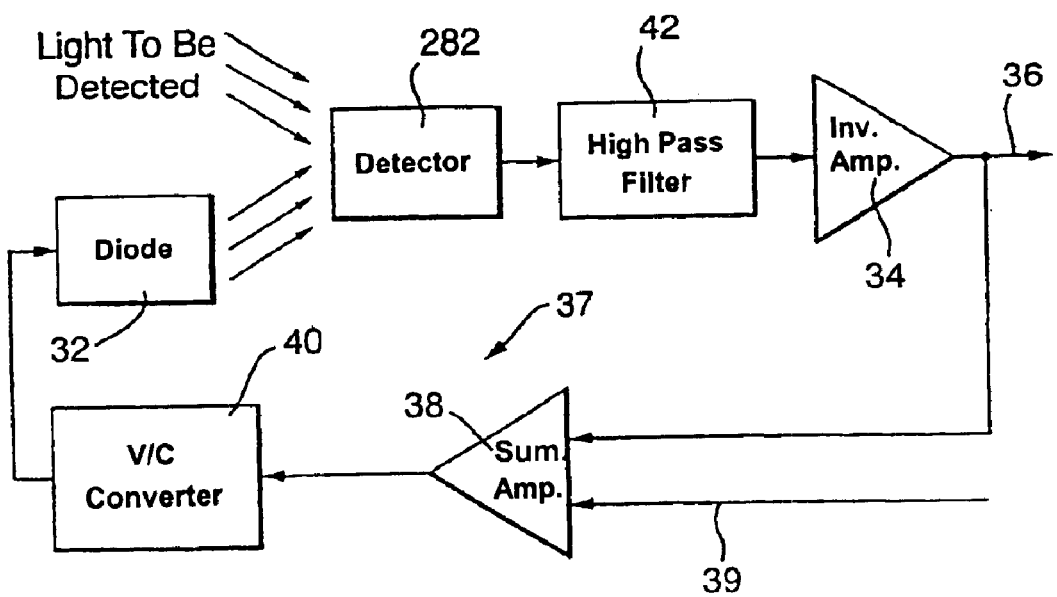
FIG. 4 is a block diagram showing another embodiment of the present invention.

FIGS. 3 and 4 show different embodiments of arrangements for controlling the diodes 32, 30 and thus for stabilising the outputs of the detectors 282, 242. For the sake of simplicity, only the arrangements for the diode 32 and the detector 282 will be described in each case, but it is to be understood that the same arrangement will be employed for the diode 30 and the detector 242.

Referring firstly to FIG. 3, the detector 282 is arranged to generate an output signal, which is amplified by an inverting amplifier 34 and supplied as a voltage output signal to an output 36. A proportion of the signal supplied to the output 36 is fed back by way of a feedback circuit 37 to the diode 32. More particularly, the feedback circuit 37 includes a summing amplifier 38 having one input connected to receive the voltage signal fed back from the output 36 and another input arranged to receive a bias voltage supplied on a line 39. The output of the summing amplifier 38 is connected to a voltage-to-current converter 40 whose output controls the diode 32.

When the magnitude of the output signal from the detector 282 begins to increase, due to an increase in the intensity of light at the measurement or reference wavelength being received thereby, the current supplied to the GaAs diode 32 begins to drop so as to reduce the intensity of the illumination emitted by the diode 32. The feedback circuit 37 thus acts as a negative feedback loop and seeks to maintain the overall illumination irradiating the detector 282, i.e. the combined illumination that is reflected back from the sample 22 and that is emitted by the GaAs diode 32, at a substantially constant predetermined level.

The predetermined level is set to correspond to the maximum external illumination level expected to be encountered by the measuring gauge in service, and is obtained by calibrating the GaAs diode 32, by appropriate selection of the bias voltage on the line 39, to emit a flux corresponding to this radiation in conditions when no radiation at a measuring or reference wavelength will be falling on the detector 282. The effect of this is to confine the detector 282 to a particular portion of its operating response characteristic and hence very much to reduce the changes in the overall radiation incident on the detector 282.

The voltage output signal which is obtained at the output 36 effectively corresponds to an error signal representing the difference between the pre-determined level and the actual level of radiation currently incident on the detector 282. This difference in turn represents the amount of light that has been reflected back from the sample 22. Such error signal is then processed in known manner to provide an indication of the parameter to be measured.

FIG. 4 shows an improvement over the arrangement shown in FIG. 3, in which the detector 282 is not required to operate in such a saturated condition. Like parts are designated by the same reference numerals as in FIG. 3.

In the circuit illustrated in FIG. 4, the detector 282 is connected to the amplifier 34 by way of a high pass filter 42. The filter 42 is arranged to pass signals at the frequencies normally generated in use of the measuring gauge through selection of a desired filter data rate. At the same time, however, the filter 42 is arranged to filter out any low frequency variations generated in response to very gradual changes, for example, in the ambient temperature or in the steady state ambient lighting.

In this embodiment, the bias voltage applied to the line 39 is set so as to maintain the level of radiation falling on the detector 282 at an amount representing the highest variation of flux expected in service. This level will naturally be considerably lower than the saturation level employed in the FIG. 3 embodiment. The present embodiment thus seeks simply to minimise variations in the overall illumination irradiating the detector 282, rather than to maintain the overall illumination level at a predetermined fixed level.

As before, the voltage signal obtained at the output 36 constitutes an error signal representing the difference between the pre-set level and the actual level of radiation incident on the detector 282.

This difference represents the amount of light falling on the detector 282 that is reflected back from the sample 22.

The circuit illustrated in FIG. 3 results in the detector 282 operating in a predetermined region of its operating response characteristic, while the circuit illustrated in FIG. 4 results in the detector 282 operating in a restricted range along its operating characteristic. In both cases, experiments have demonstrated that the detector benefits from an improved linearity and extended frequency response.

Figure 5:
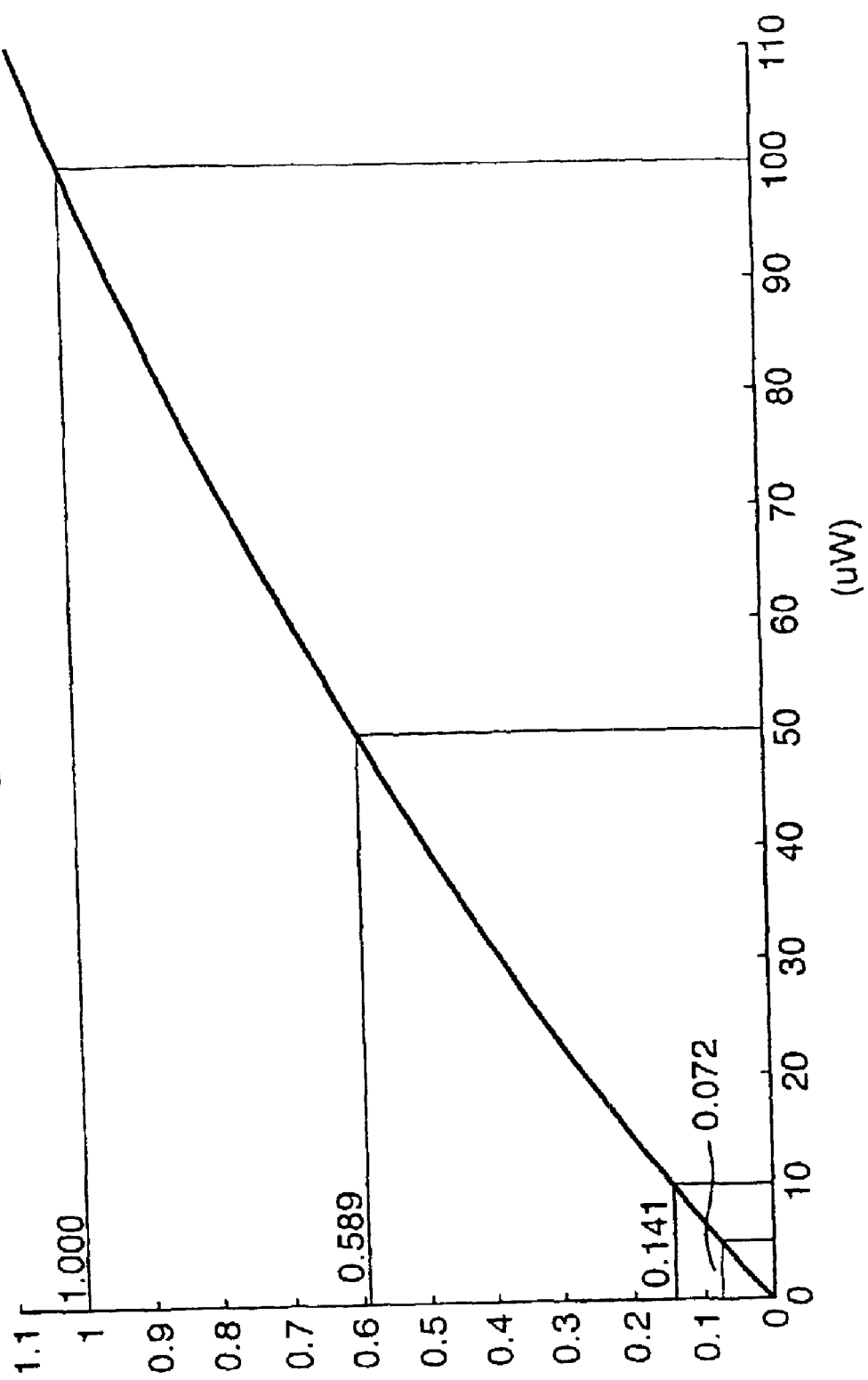
FIG. 5 is a graph showing the non-linearity of the response of a conventional PbS detector.

FIG. 5 shows a graph representing the response of a conventional detector in dependence upon incident radiation for the full operating range of the detector. The optical power of the incident radiation is represented along the X axis and the normalised response of the detector is represented along the Y axis. As shown, the detector response is 0.072 at 5 $\mu$W of incident radiation and is 0.141 at 10 $\mu$W of incident radiation, and hence in this region of the curve the detector response is almost linear. However, making the same comparison for 50 $\mu$W and 100 $\mu$W of incident radiation, the detector response is in the ratio of 0.589:1.000, which is far from linear.

The curve shown in FIG. 5 demonstrates that the smaller the change in incident radiation on the detector the more linear the detector signal.

Consequently, since the feedback arrangement according to the present invention reduces the changes in the overall radiation incident on the detector, the resultant signals generated by the detector will be more linear.

This is especially advantageous in situations where the detector is strongly illuminated in operation and deep absorptions are likely, since then a linearised response is essential to ensure proper calibration and good temperature stability.

Figure 6:
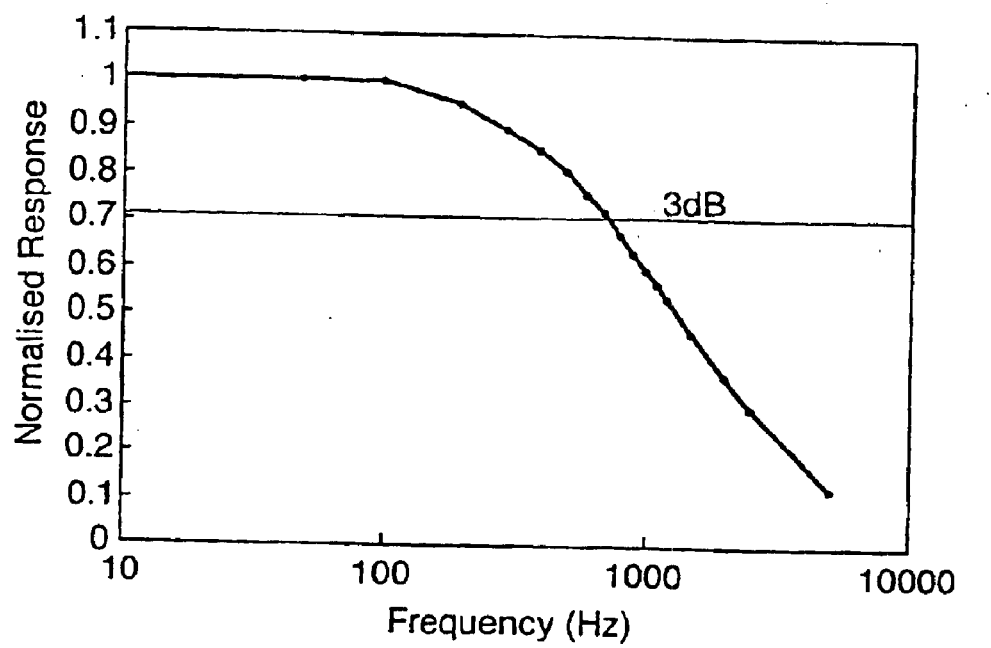
FIG. 6 is a graph representing the frequency response of a PbS detector in a known gauge.

FIG. 6 shows a graph of frequency response for a conventional PbS detector in a known measuring gauge at room temperature. The normalised response of the detector is plotted against the chopping frequency of the incident radiation, which corresponds to the frequency of rotation of the filter wheel 14 shown in FIG. 1 multiplied by the number of filters in the filter wheel 14.

As can be seen, the response of the detector is constant for frequencies up to approximately 100 Hz and reaches a −3 db point, at which typically signals suffer a phase shift of 90°, at approximately 700 Hz.

Figure 7:
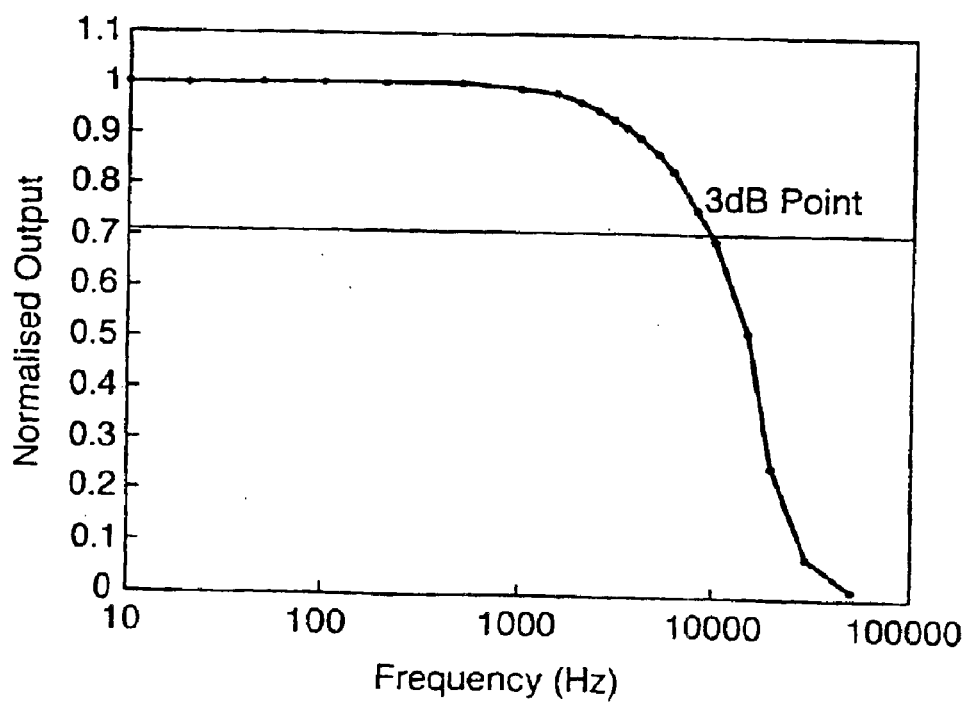
FIG. 7 is a graph showing the frequency response of a detector when the present invention is employed.

Turning now to FIG. 7, this represents the detector frequency response for a detector operated according to the present invention. As can be seen, the frequency response of the detector is effectively constant for chopping frequencies up to approximately 1,000 Hz, and the −3 db point occurs at approximately 10 kHz The frequency response is thus significantly improved.

In practice, the use of the feedback arrangement according to the present invention effectively reduces the magnitude of the signal generated by the detector 282 for amplification by the main amplifier 34 for output, and this may result in the introduction of additional noise during amplification. However, by controlling the level of feedback by appropriate selection of the gain of the amplifier 38 in the feedback path, the extension of the frequency response of the detector can be optimally selected according to the application.

It is envisaged that extension of the frequency response of the detector will enable measurement times for each measurement and reference wavelength of as little as 1 ms and less, which is significantly faster than is currently possible.

This decrease in response time is particularly advantageous in scanning applications in which a travelling web of material is scanned in order to obtain measurement wavelengths, since the results for each scan may be averaged to give excellent cross web resolution. The improved response time, is also advantageous when the sample whose parameter to be measured comprises a material, such as snack foods and tobacco, susceptible of generating presentation noise, which is due to changes in the product height, reflectivity, and angle with movement. In this instance, the fast acquisition of wavelength data may permit a significant reduction in the presentation noise.

The above description has been confined to the operation of the detector 282 and the diode 32 for providing an output signal representing the light reflected back from the sample 22. It will be appreciated that the operation of the detector 242 and diode 30 for providing an output signal representing the light from the lamp 12 as filtered by the filter wheel 14 is similar. Both such signals are then processed in a known manner for determining the parameter to be measured.

Various modifications are possible in the described arrangement

In particular, each of the diodes 30 or 32 may be replaced by an array of such diodes equip-spaced about the associated detector 242 or 282 in order to ensure even illumination of the detector.

Further, the diodes 30, 32 may be arranged to illuminate the detectors 24, 28 directly, rather than by means of reflection from the blocking filters 244, 284 as described.

It has been assumed in the above description that the detectors 242, 282 are PbS detectors and that the diodes 30, 32 are GaAs diodes. However, other kinds of detector may also be employed together with appropriate diodes.

In addition, it will be appreciated that the amplifiers 34, 38 can be replaced by alternative amplifier arrangements providing that the feedback circuit 37 still acts to reduce the current supplied to the diode 30, 32 when the intensity of light irradiating the detector 242, 282 increases.

The invention has been described in relation to an infrared measuring gauge but it may also be employed in a measuring gauge utilising other wavelengths of light, for example utilising wavelengths of visible light.

Indeed, the invention may also be applied to other kinds of electromagnetic, particularly infrared, detection apparatus, for example to an infrared temperature detector or to infrared imaging apparatus.

What is claimed is:

1. An infrared gauge for measuring a parameter of a sample, comprising:
    a main source of infrared radiation for illuminating the sample,
    a detector circuit including a detector for detecting infrared radiation received from the sample and for generating a signal representing the radiation received, and
    means for stabilizing a response characteristic of the detector to the radiation received, said stabilizing means comprising:
    a controlled source of additional infrared radiation for directing radiation at the detector, and
    means for controlling the source of additional radiation in dependence upon the signal generated by the detector.

2. An infrared gauge according to claim 1 in which the stabilizing means are arranged to linearise the response of the detector to the radiation received.

3. An infrared gauge according to claim 1 in which the stabilizing means are arranged to extend the frequency response of the detector to the radiation received.

4. An infrared gauge according to claim 1 in which the controlling means are arranged to adjust the intensity of the radiation emitted by the controlled source in dependence upon the signal generated by the detector.

5. An infrared gauge according to claim 1 in which the controlling means are arranged to adjust the intensity of the radiation emitted by the controlled source so as to maintain overall illumination of the detector at a substantially predetermined level.

6. An infrared gauge according to claim 1 in which the controlling means are arranged to adjust the intensity of the radiation emitted by the controlled source so as to minimize variations in the overall illumination of the detector.

7. An infrared gauge according to claim 1 in which the controlling means provide a feedback path from an output of the detector circuit to the controlled source.

8. An infrared gauge according to claim 7 in which the detector circuit is arranged to supply a voltage output signal and in which the controlling means comprise a voltage to current converter.

9. An infrared gauge according to claim 7 in which the detector circuit comprises an amplifier arranged to receive the detector signal.

10. An infrared gauge according to claim 1 in which the detector circuit comprises a high pass filter arranged to receive the detector signal.

11. An infrared gauge according to claim 1 in which the controlled source is arranged to irradiate the detector by way of a reflective surface.

12. An infrared gauge according to claim 1 in which the controlled source is arranged to irradiate the detector directly.

13. An infrared gauge according to claim 1 comprising a plurality of the controlled sources arranged to provide an even distribution of radiation for irradiating the detector.

14. An infrared gauge according to claim 1 in which the main source of radiation and the detector are arranged to co-operate such that the detector detects radiation transmitted, scattered or reflected by the sample following irradiation by the said main source.

15. An infrared gauge according to claim 1 further comprising a secondary detector circuit including a secondary detector for detecting infrared radiation and for generating a signal representing the radiation received, a further controlled source of additional infrared radiation for directing radiation at the secondary detector, and means for controlling the further source of additional radiation in dependence upon the signal generated by the secondary detector.

16. An infrared gauge according to claim 7 further comprising means responsive to the signal generated by the detector circuit and the signal generated by the secondary detector circuit, respectively, for calculating the parameter to be measured.

17. An infrared gauge according to claim 9 in which the gain of the amplifier is selected to as to control the level of the feedback signal whereby to extend the frequency response of the detector.

* * * * *